(12) United States Patent
Douglas et al.

(10) Patent No.: US 11,514,655 B1
(45) Date of Patent: Nov. 29, 2022

(54) METHOD AND APPARATUS OF PRESENTING 2D IMAGES ON A DOUBLE CURVED, NON-PLANAR DISPLAY

(71) Applicants: Robert Edwin Douglas, Winter Park, FL (US); David Byron Douglas, Winter Park, FL (US)

(72) Inventors: Robert Edwin Douglas, Winter Park, FL (US); David Byron Douglas, Winter Park, FL (US)

(\*) Notice: Subject to any disclaimer, the term of this patent is extended or adjusted under 35 U.S.C. 154(b) by 0 days.

(21) Appl. No.: 17/561,961

(22) Filed: Dec. 26, 2021

Related U.S. Application Data (63) Continuation-in-part of application No. 17/228,659, filed on Apr. 12, 2021, now Pat. No. 11,210,785, which is a continuation-in-part of application No. 17/072,350, filed on Oct. 16, 2020, now Pat. No. 11,003,948, which is a continuation-in-part of application No. 16/842,631, filed on Apr. 7, 2020, now Pat. No. 11,003,342.

(60) Provisional application No. 63/010,004, filed on Apr. 14, 2020, provisional application No. 62/916,262, filed on Oct. 17, 2019.

(51) Int. Cl.
| | |
|---|---|
| *G06T 19/00* | (2011.01) |
| *G06F 3/01* | (2006.01) |
| *G06F 3/0346* | (2013.01) |
| *G09G 3/00* | (2006.01) |

(52) U.S. Cl.
CPC ............ *G06T 19/006* (2013.01); *G06F 3/012* (2013.01); *G06F 3/013* (2013.01); *G06F 3/0346* (2013.01); *G09G 3/03* (2020.08)

(58) Field of Classification Search
CPC .............................. H04N 13/344; G02B 27/017
See application file for complete search history.

(56) References Cited

U.S. PATENT DOCUMENTS

| | | | |
|---|---|---|---|
| 10,154,562 B1* | 12/2018 | Baloga | H05B 33/145 |
| 2014/0333532 A1* | 11/2014 | Ohbitsu | G06F 3/013 |
| | | | 345/156 |
| 2020/0296354 A1* | 9/2020 | Bickerstaff | G02B 27/017 |

\* cited by examiner

*Primary Examiner* — Ross Varndell (57) ABSTRACT

This patent includes a method for displaying a 2D image on a non-planar display with a top portion of said non-planar display curving inwards towards a user's viewing position, a bottom portion of said non-planar display curves inwards towards said user's viewing position, a left portion of said non-planar display curves inward towards said user's viewing position and a right portion of said non-planar display curves inward towards said user's viewing position. This type of display can be used as a virtual display for extended reality head display units including virtual reality, augmented reality or mixed reality displays. For a virtual display, advanced features can be performed including stereoscopic viewing the screen with a convergence point shifting technique, zooming and rotating to maximize usability. The virtual display can be modified in its horizontal curvature or vertical curvature per user preference. The non-planar display can be a tangible TV, monitor, phone or tablet as discussed in this patent.

20 Claims, 11 Drawing Sheets

TANGIBLE NON-PLANAR DISPLAY

A NON-PLANAR DISPLAY

A non-planar display comprises:
- a top portion of said non-planar display curves inwards towards a user's viewing position;
- a bottom portion of said non-planar display curves inwards towards said user's viewing position;
- a left portion of said non-planar display curves inward towards said user's viewing position; and
- a right portion of said non-planar display curves inward towards said user's viewing position.

TANGIBLE NON-PLANAR DISPLAY

VIRTUAL NON-PLANAR DISPLAY

Virtual display options:
- Types of display units: augmented reality; virtual reality; and mixed reality
- Key components of display units
  - a processor
  - a power supply
  - an inertial measurement unit configured to determine an orientation of the display unit
  - a transmit/receive element configured to receive signals from a set of transmitters in an area wherein the received signals are used to compute a location of the display unit within the area
  - a left eye display operably connected to the processor
  - a right eye display operably connected to the processor
  - a non-transitory memory configurable to have computer-executable instructions stored thereupon, which when executed by the processor cause the display unit to display a 2D image to a user on a non-planar display

USING MULTIPLE CONVERGENCE POINTS ON THE DOUBLE CURVED NON-PLANAR DISPLAY

Fig. 7A

| |
|---|
| Moving the virtual display from a first location within virtual space to a second location within virtual space wherein said first location is different from said second location 700 |

↓

| |
|---|
| Generating new a left eye image for a left eye display of said extended reality headset based on said left eye viewpoint, a viewing angle and said second location of said virtual display 701 |

↓

| |
|---|
| Generating a right eye image for a right eye display of said extended reality headset based on said right eye viewpoint, said viewing angle and said second location of said virtual display 702 |

↓

| |
|---|
| Displaying said left eye image for said left eye display of said extended reality headset 703 |

↓

| |
|---|
| Displaying said right eye image for said right eye display of said extended reality headset 704 |

RE-SIZING A DOUBLE CURVED NON-PLANAR DISPLAY WITHIN VIRTUAL SPACE

RE-SHAPING A NON-PLANAR DISPLAY WITHIN VIRTUAL SPACE

MOVING A DOUBLE CURVED NON-PLANAR DISPLAY WITHIN
VIRTUAL SPACE

MAPPING A 2D IMAGE ONTO A DOUBLE CURVED NON-PLANAR DISPLAY

METHOD AND APPARATUS OF PRESENTING 2D IMAGES ON A DOUBLE CURVED, NON-PLANAR DISPLAY

CROSS REFERENCE TO RELATED APPLICATIONS

This application is a continuation in part of U.S. patent application Ser. No. 17/228,659 filed on Apr. 12, 2021, which is a continuation in part of U.S. patent application Ser. No. 17/072,350 filed on Oct. 16, 2020, which is a continuation in part of U.S. patent application Ser. No. 16/842,631 filed on Apr. 7, 2020, which claims the benefit of U.S. Provisional 62/916,262 filed on Oct. 17, 2019. U.S. application Ser. No. 17/228,659 also claims the benefit of U.S. Provisional 63/010,004 filed on Apr. 14, 2020.

TECHNICAL FIELD

Aspects of this disclosure are generally related to image analysis.

INTRODUCTION

Multiple monitor setups can be used.

SUMMARY

All examples, aspects and features mentioned in this document can be combined in any technically conceivable way.

In this patent, a non-planar display with a double curvature is taught. The preferred design is in U.S. Ser. No. 29/721,280 filed on Jan. 20, 1920. A double curvature means both a horizontal curvature and a vertical curvature. This concept can be applied to tangible monitors and virtual monitors as would be viewed on an extended reality head display unit. The types of extended reality displays include: augmented reality; virtual reality; and mixed reality. The key components in the extended reality head display units include: a processor; a power supply; an inertial measurement unit configured to determine an orientation of the display unit; a transmit/receive element configured to receive signals from a set of transmitters in an area wherein the received signals are used to compute a location of the display unit within the area; a left eye display operably connected to the processor; a right eye display operably connected to the processor; a non-transitory memory configurable to have computer-executable instructions stored thereupon, which when executed by the processor cause the display unit to display a 2D image to a user on a non-planar display.

Some embodiments comprise generating stereoscopic images of a virtual double curved non-planar monitor. Some embodiments comprise wherein the stereoscopic images are generated from different viewpoints. Some embodiments comprise generating stereoscopic images using convergence point techniques. Some embodiments comprise using multiple convergence points on the double curved non-planar monitor. Some embodiments comprise re-sizing the double curved non-planar monitor. Some embodiments comprise re-shaping the double curved non-planar monitor. Some embodiments comprise moving the double curved non-planar monitor. Some embodiments comprise, for pixels (i,j) in a 2D image, assigning (x,y,z) coordinates in virtual space. Some embodiments comprise using single frame 2D images from photos, text documents, or drawings. Some embodiments comprise using a 2D image as a frame from a video.

Some of the techniques in this patent are performed in conjunction with techniques disclosed in the following patents (all of which are incorporated by reference in their entirety): U.S. patent application Ser. No. 15/878,463, Interactive 3D cursor for use in medical imaging; U.S. patent application Ser. No. 16/010,925, Interactive placement of a 3D digital representation of a surgical device or anatomic feature into a 3D radiologic image for pre-operative planning; U.S. patent application Ser. No. 15/904,092, Processing 3D medical images to enhance visualization; U.S. patent application Ser. No. 15/949,202, Smart operating room equipped with smart surgical devices; U.S. Pat. No. 9,473,766, Method and apparatus for three dimensional viewing of images; U.S. Pat. No. 9,615,806, Method and apparatus for creation and display of artifact corrected three dimensional (3D) volumetric data from biplane fluoroscopic image acquisition; U.S. patent Ser. No. 14/644,489, Method and apparatus for creation and display of artifact corrected three dimensional (3D) volumetric data from biplane fluoroscopic image acquisition; U.S. Pat. No. 9,980,691, Method and apparatus for three dimensional viewing of images; U.S. Pat. No. 9,349,183, Method and apparatus for three dimensional viewing of images; U.S. patent application Ser. No. 16/195,251, Interactive voxel manipulation in volumetric medical imaging for virtual motion, deformable tissue, and virtual radiological dissection; U.S. patent application Ser. No. 16/509,592, Implantable markers to aid surgical operations; U.S. patent application Ser. No. 16/524,275, Using geo-registered tools to manipulate three-dimensional medical images; PCT/US19/478, A virtual tool kit for radiologists; U.S. patent application Ser. No. 16/563,985, A method and apparatus for the interaction of virtual tools and geo-registered tools; U.S. patent application Ser. No. 16/594,139, Method and apparatus for performing 3D imaging examinations of a structure under different configurations and analyzing morphologic changes; U.S. patent application Ser. No. 16/683,256, Method and apparatus for performing 3D imaging examinations of a structure under different configurations and analyzing morphologic changes; U.S. patent application Ser. No. 16/703,629, Radiologist-assisted machine learning with volume-subtending 3D cursor; PCT/US19/239, Radiologist-assisted machine learning with interactive, volume-subtending 3D cursor; U.S. provisional application No. 62/843,612, A method of creating a computer-generated patient specific image; U.S. provisional application No. 62/846,770, A method of prioritized volume rendering to improve visualization of prioritized items within a 3D volume; U.S. provisional application No. 62/850,002, A method of creating an artificial intelligence generated differential diagnosis and management recommendation tool boxes during medical personnel analysis and reporting; U.S. patent application Ser. No. 16/654,047, A method to modify imaging protocols in real time through implementation of artificial intelligence; US provisional application No. 62/856,185, A method of image manipulation based on eye tracking; U.S. patent application Ser. No. 16/506,073, A method for illustrating direction of blood flow via pointers; U.S. patent application No. 62/906,125, A method and apparatus for stereoscopic rendering of mobile fluids; and, U.S. patent application No. 62/939,685, Method and apparatus for development of an organ-specific coordinate system.

DETAILED DESCRIPTIONS

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

Figure 1A:
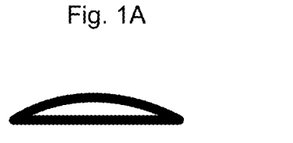
FIG. 1A is a top view of a non-planar display.

FIG. 1A is a top view of a non-planar display.

Figure 1B:
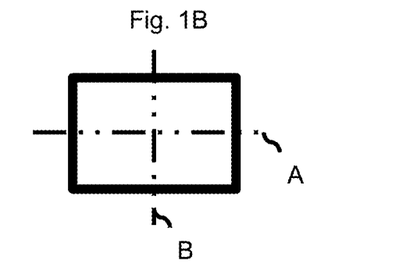
FIG. 1B is a front view of the non-planar display shown in FIG. 1A.

FIG. 1B is a front view of the non-planar display shown in FIG. 1A. Note a cross-section taken along line A. Note a cross-section taken along line B.

Figure 1C:
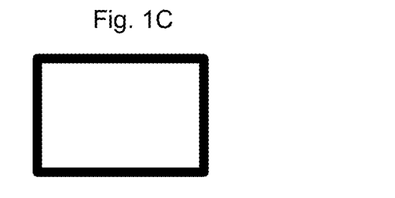
FIG. 1C is a rear view of the non-planar display shown in FIG. 1A.

FIG. 1C is a rear view of the non-planar display shown in FIG. 1A.

Figure 1D:
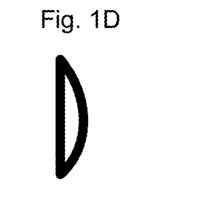
FIG. 1D is the right side view of the non-planar display screen shown in FIG. 1A.

FIG. 1D is the right side view of the non-planar display screen shown in FIG. 1A.

Figure 1E:
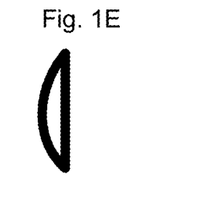
FIG. 1E is the left side view of the non-planar display screen shown in FIG. 1A.

FIG. 1E is the left side view of the non-planar display screen shown in FIG. 1A.

Figure 1F:
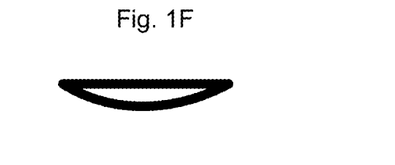
FIG. 1F is the bottom view of the non-planar display screen shown in FIG. 1A.

FIG. 1F is the bottom view of the non-planar display screen shown in FIG. 1A.

Figure 1G:
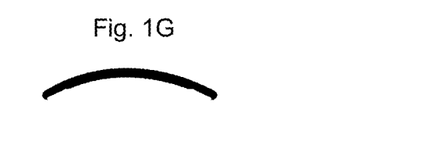
FIG. 1G is a cross-sectional view taken along line A in FIG. 1B.

FIG. 1G is a cross-sectional view taken along line A in FIG. 1B.

Figure 1H:
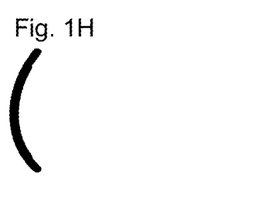
FIG. 1H is a cross-sectional view taken along line B in FIG. 1B.

FIG. 1H is a cross-sectional view taken along line B in FIG. 1B. The device is not limited to the scale shown herein. Also note that the top, bottom, left and right sides of the monitor can be comprised of straight edges or curved edges. The uniqueness of this design is the "double curved" appearance. Note that the top portion of the monitor curves inwards towards the user. Note that the bottom portion of the monitor curves inwards towards the user. Note that the left portion of the monitor curves inward towards the user. Note that the right portion of the monitor curves inward towards the user. Different portions of the monitor would be roughly the same distance from the user's head. This solves the problem of having numerous (e.g., 8+) monitors lined up for a single user and the monitors in the center are easily seen at the best viewing distance and the monitors on the sides are poorly seen due to longer viewing distances.

Figure 1I:
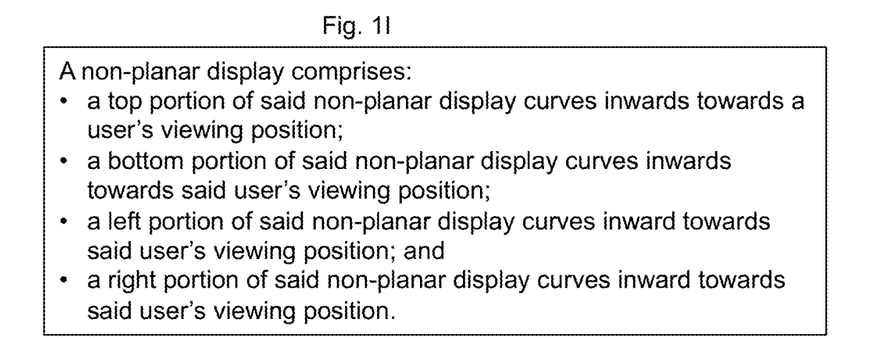
FIG. 1I is a text box describing a non-planar display in this patent.

FIG. 1I is a text box describing a non-planar display in this patent. A non-planar display comprises wherein a top portion of said non-planar display curves inwards towards a user's viewing position, a bottom portion of said non-planar display curves inwards towards said user's viewing position, a left portion of said non-planar display curves inward towards said user's viewing position, and a right portion of said non-planar display curves inward towards said user's viewing position. In some embodiments, the 2D image can be derived from imagery as described in Ser. No. 17/225,610 filed on Apr. 8, 2021, AN IMPROVED IMMERSIVE VIEWING EXPERIENCE, which is incorporated by reference in its entirety and Ser. No. 17/237,152 filed on Apr. 22, 2021, AN IMPROVED IMMERSIVE VIEWING EXPERIENCE, which is incorporated by reference in its entirety. Some embodiments comprise using a camera with a synchronized scanning laser range finder (CSLRF) which covers an area corresponding to the selected field of view of the camera, so that the depth of field could be recorded along with the actual RBG colors for that point in space. Some embodiments comprise using a CSLRP for a left image and a CSLRF for the right image to yield improve stereoscopic imagery.

Figure 2A:
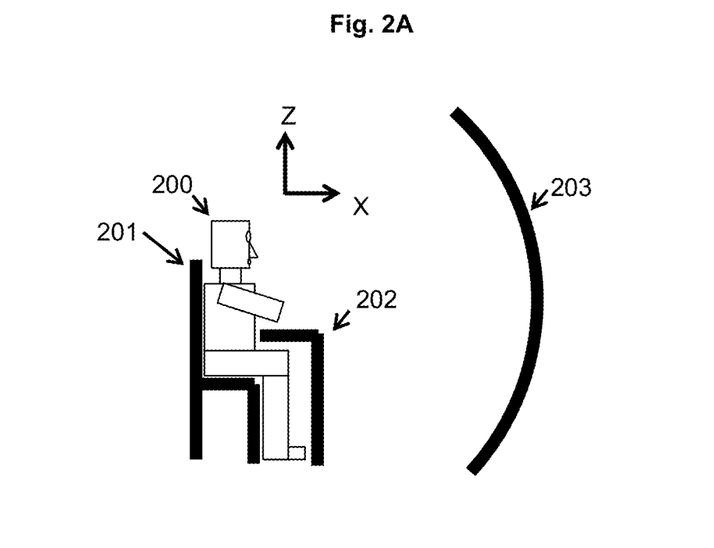
FIG. 2A illustrates a side view of the a user sitting at a non-planar display.

FIG. 2A illustrates a side view of the a user sitting at a non-planar display. 200 illustrates a user. 201 illustrates a chair that the user 200 is sitting on. 202 illustrates a desk that the user is using. 203 illustrates a monitor wherein the top portion of the monitor curves toward the user and the bottom of the monitor curves toward the user. A coordinate system is also shown wherein the Z-direction is vertical (i.e., upward/downward direction towards the floor) and the X-direction is horizontal in the direction from the user to the monitor 203. Note that this can be in the form of a TV or monitor. Some embodiments comprise a double curved tablet or phone.

Figure 2B:
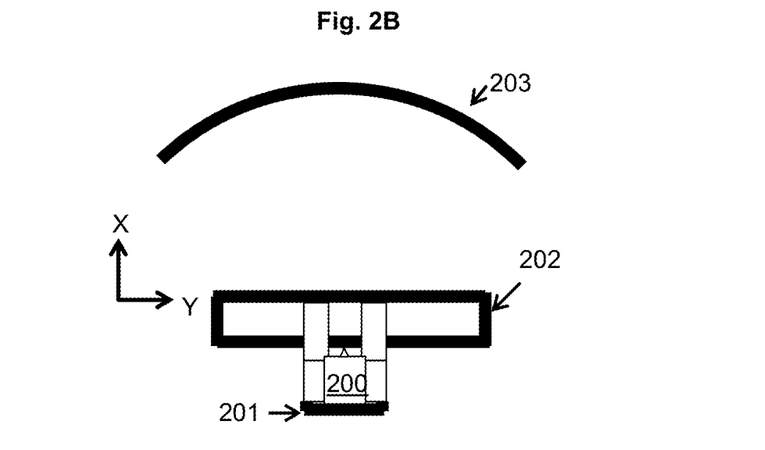
FIG. 2B illustrates a top-down view of the user's workstation.

FIG. 2B illustrates a top-down view of the user's workstation. 200 illustrates the user. 201 illustrates a chair that the user 200 is sitting on. 202 illustrates a desk that the user is using. 203 illustrates a monitor wherein the left portion of the monitor curves toward the user and the right portion of the monitor curves toward the user. A coordinate system is also shown wherein the Y-direction is horizontal in the left-right direction and the X-direction is horizontal in the direction from the user to the monitor 203. 20. The display would comprise: a processor; a non-planar screen; and a non-transitory memory configurable to have computer-executable instructions stored thereupon, which when executed by the processor cause the display to display a 2D image to a user on a non-planar screen wherein: a top portion of said non-planar screen curves inwards towards a user; the bottom portion of said non-planar screen curves inwards towards the user; the left portion of said non-planar screen curves inward towards the user; and, the right portion of said non-planar screen curves inward towards the user.

Figure 3A:
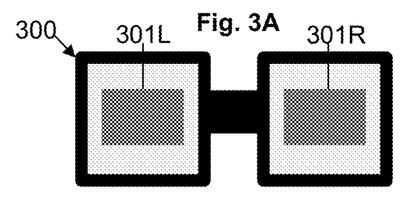
FIG. 3A illustrates a virtual non-planar display viewed from the front.

FIG. 3A illustrates a virtual non-planar display viewed from the front. 300 illustrates an extended reality head display unit. 301L illustrates a left eye image of the non-planar virtual display viewed from the front. 301R illustrates a right eye image of the non-planar virtual display viewed from the front.

Figure 3B:
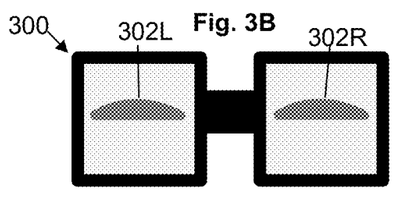
FIG. 3B illustrates a virtual non-planar display viewed from the top.

FIG. 3B illustrates a virtual non-planar display viewed from the top. 300 illustrates an extended reality head display unit. 302L illustrates a left eye image of the non-planar virtual display viewed from the top. 302R illustrates a right eye image of the non-planar virtual display viewed from the top.

Figure 3C:
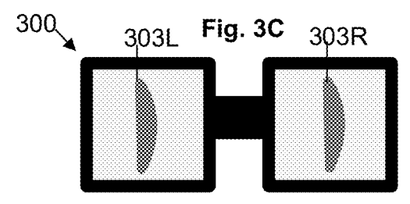
FIG. 3C illustrates a virtual non-planar display viewed from the right side.

FIG. 3C illustrates a virtual non-planar display viewed from the right side. 300 illustrates an extended reality head display unit. 303L illustrates a left eye image of the non-planar virtual display viewed from the right side. 303R illustrates a right eye image of the non-planar virtual display viewed from the right side.

Figure 3D:
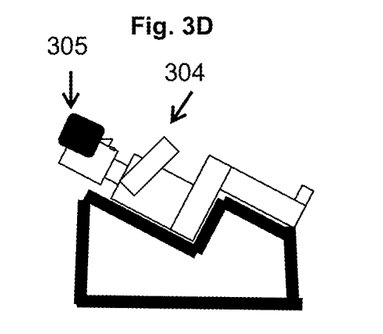
FIG. 3D illustrates a user laying in a lazy boy recliner wearing an extended reality display.

FIG. 3D illustrates a user laying in a lazy boy recliner wearing an extended reality display. 304 illustrates the user. 305 illustrates an extended reality head display unit.

Figure 3E:
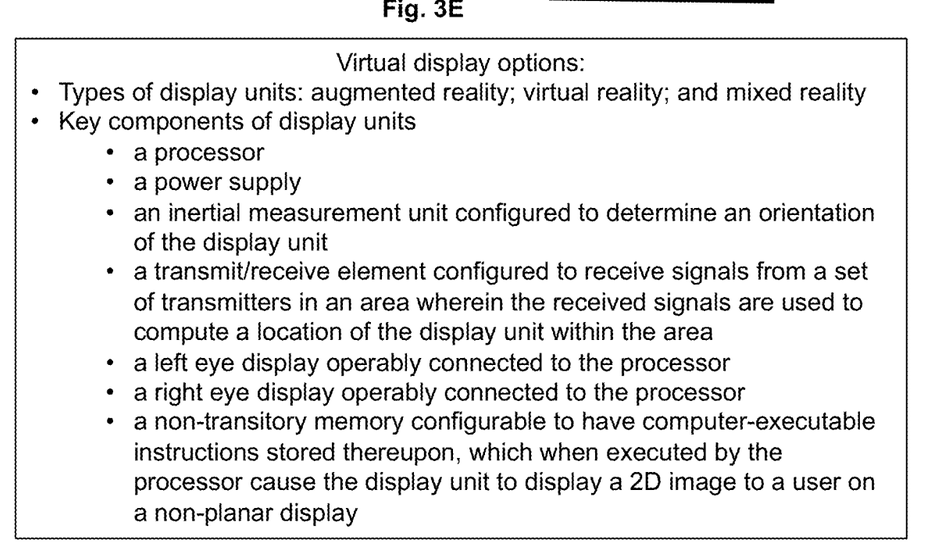
FIG. 3E illustrates a text box showing virtual non-planar display options.

FIG. 3E illustrates a text box showing virtual non-planar display options. The types of extended reality head display units include, but are not limited to, the following: augmented reality (AR); virtual reality (VR); and, mixed reality (MR). The key components of display units include: a processor; a power supply; an inertial measurement unit configured to determine an orientation of the display unit; an eye tracking system; a transmit/receive element configured to receive signals from a set of transmitters in an area wherein the received signals are used to compute a location of the display unit within the area; a left eye display operably connected to the processor; a right eye display operably connected to the processor; a non-transitory memory configurable to have computer-executable instructions stored thereupon, which when executed by the processor cause the display unit to display a 2D image to a user on a non-planar display. The extended reality head display unit can receive its power supply from a wire or be battery driven. The content of the imagery can be received via a wire or wireless link. 2D image can be derived from imagery as described in Ser. No. 17/225,610 filed on Apr. 8, 2021, AN IMPROVED IMMERSIVE VIEWING EXPERIENCE, which is incorporated by reference in its entirety and Ser. No. 17/237,152 filed on Apr. 22, 2021, AN IMPROVED IMMERSIVE VIEWING EXPERIENCE, which is incorporated by reference in its entirety.

Figure 4:
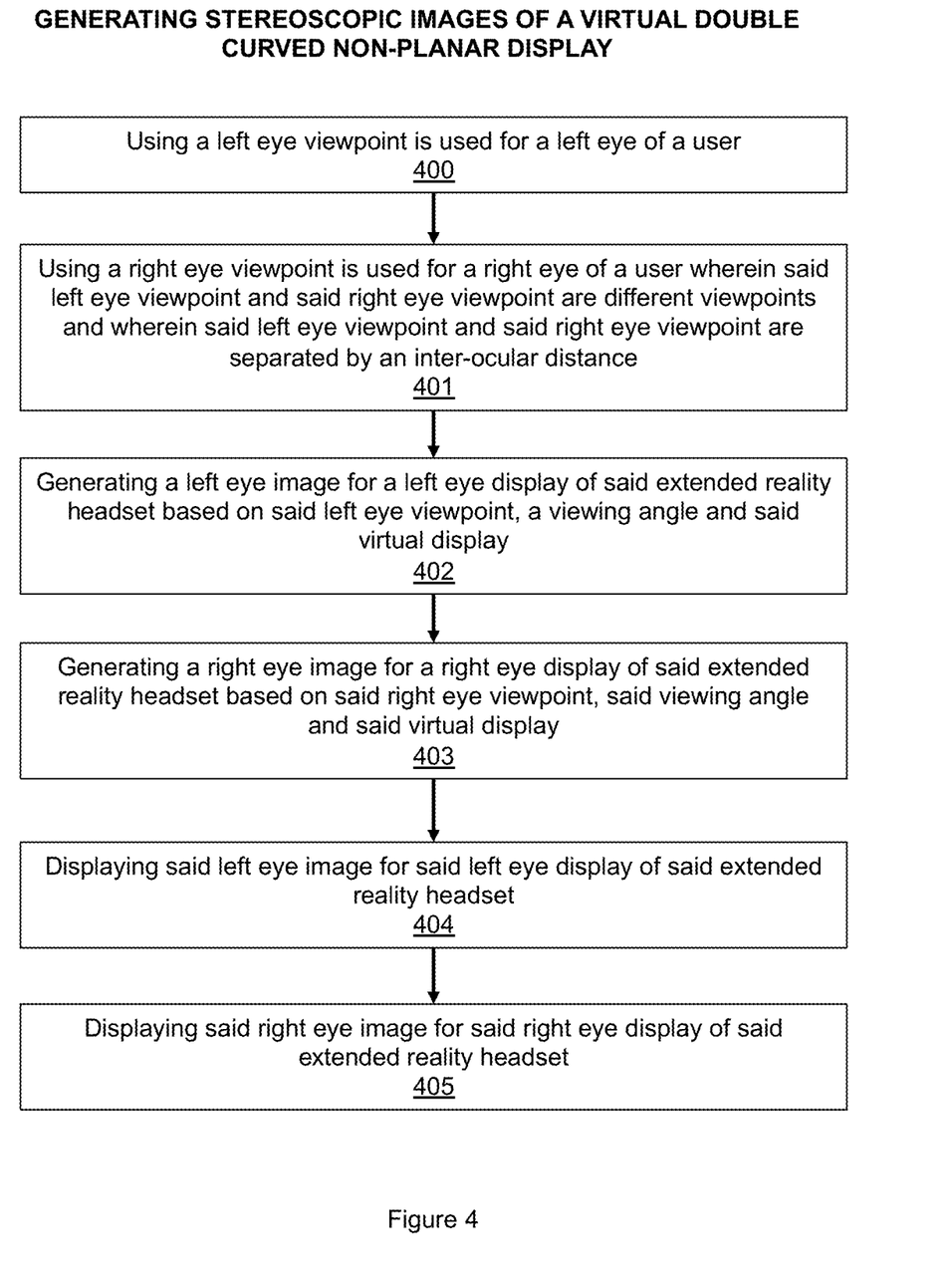
FIG. 4 illustrates generating stereoscopic images of a virtual double curved non-planar display.

FIG. 4 illustrates generating stereoscopic images of a virtual double curved non-planar display. 400 illustrates using a left eye viewpoint is used for a left eye of a user. 401 illustrates using a right eye viewpoint is used for a right eye of a user wherein said left eye viewpoint and said right eye viewpoint are different viewpoints and wherein said left eye viewpoint and said right eye viewpoint are separated by an inter-ocular distance. 402 illustrates generating a left eye image for a left eye display of said extended reality headset based on said left eye viewpoint, a viewing angle and said virtual display. 403 illustrates generating a right eye image for a right eye display of said extended reality headset based on said right eye viewpoint, said viewing angle and said virtual display. 404 illustrates displaying said left eye image for said left eye display of said extended reality headset. 405 illustrates displaying said right eye image for said right eye display of said extended reality headset.

Figure 5:
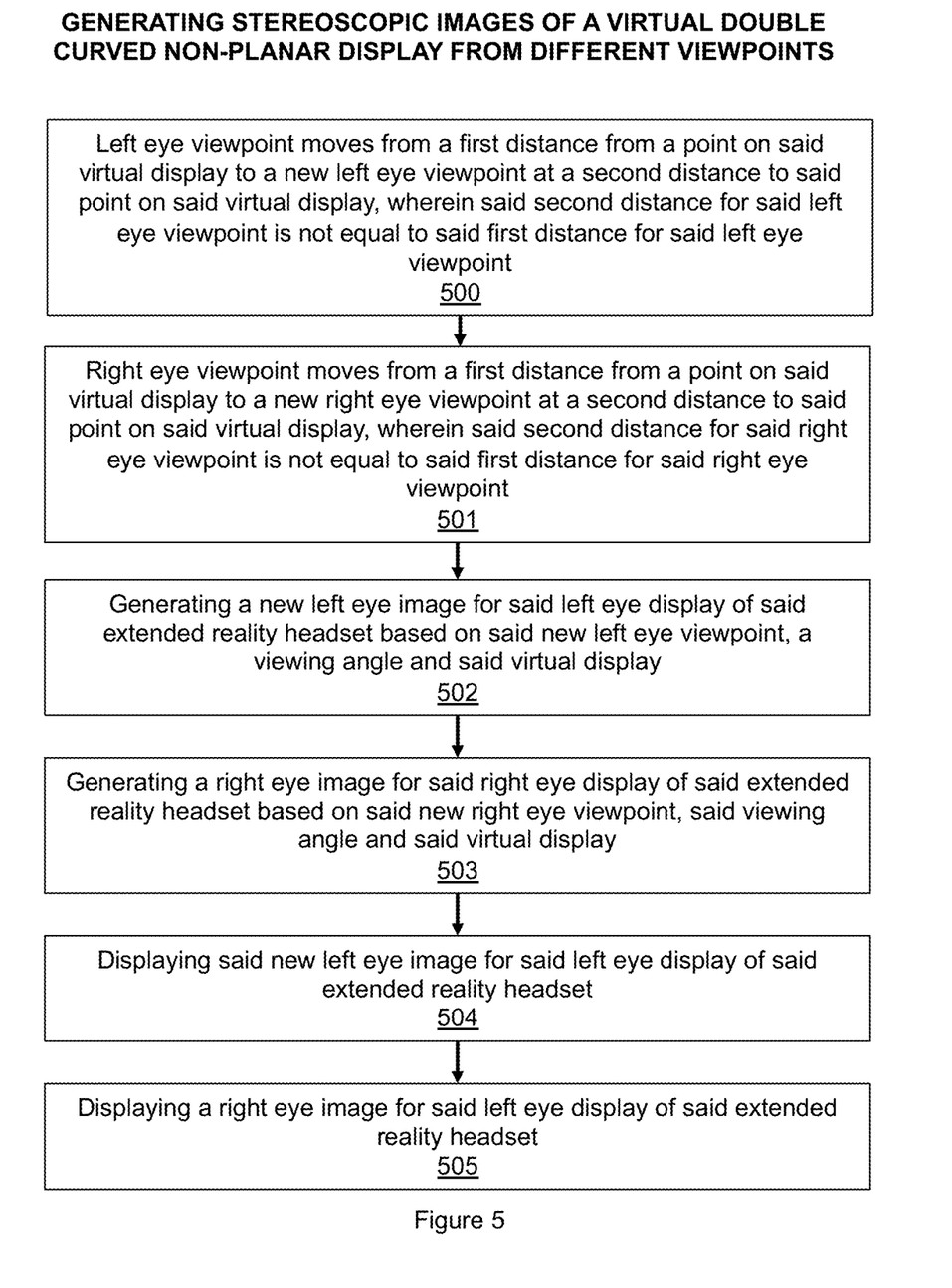
FIG. 5 illustrates generating stereoscopic images of a virtual double curved non-planar display from different viewpoints.

FIG. 5 illustrates generating stereoscopic images of a virtual double curved non-planar display from different viewpoints. 500 illustrates moving a left eye viewpoint from a first distance from a point on said virtual display to a new left eye viewpoint at a second distance to said point on said virtual display, wherein said second distance for said left eye viewpoint is not equal to said first distance for said left eye viewpoint. 501 illustrates moving a right eye viewpoint from a first distance from a point on said virtual display to a new right eye viewpoint at a second distance to said point on said virtual display, wherein said second distance for said right eye viewpoint is not equal to said first distance for said right eye viewpoint. 502 illustrates generating a new left eye image for said left eye display of said extended reality headset based on said new left eye viewpoint, a viewing angle and said virtual display. 503 illustrates generating a right eye image for said right eye display of said extended reality headset based on said new right eye viewpoint, said viewing angle and said virtual display. 504 illustrates displaying said new left eye image for said left eye display of said extended reality headset. 505 illustrates displaying a right eye image for said left eye display of said extended reality headset. This process will allow a user to perform stereoscopic zooming in or stereoscopic zooming out. This process will allow a user to perform stereoscopic panning up or panning down. This process will allow a user to perform stereoscopic shifting up or shifting down. Thus, a user can perform shifting in an x-direction, a y-direction or a z-direction. This process will allow a user to perform stereoscopic rotating up or rotating down. This process will allow a user to perform stereoscopic rotating to the left or to the right. This process will allow stereoscopically rotating forward or backwards. Thus, a user can perform rotation about an x-axis, a y-axis and a z-axis in a roll, pitch or yaw process.

Figure 6:
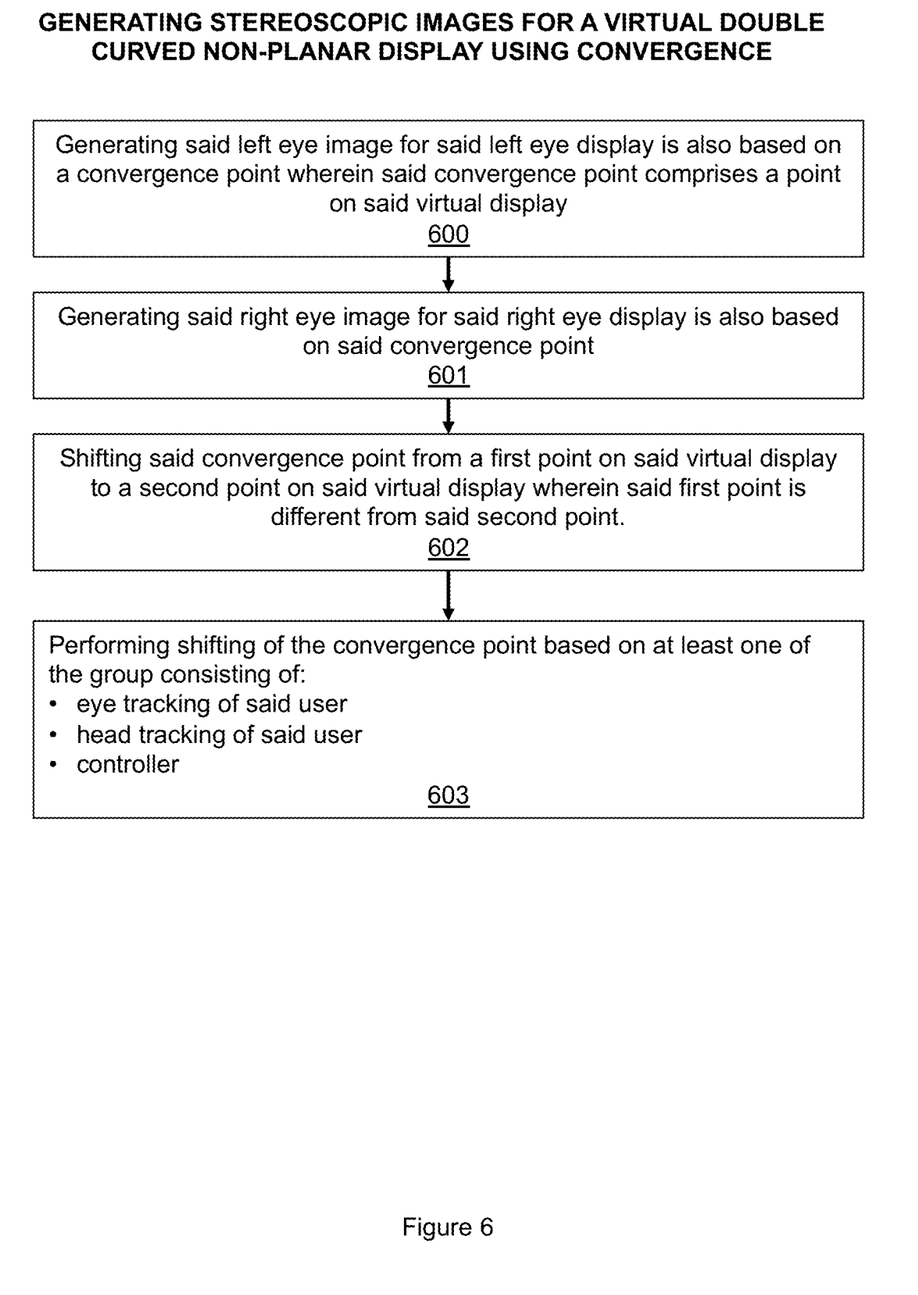
FIG. 6 illustrates generating stereoscopic images for a virtual double curved non-planar display using convergence.

FIG. 6 illustrates generating stereoscopic images for a virtual double curved non-planar display using convergence. 600 illustrates generating said left eye image for said left eye display is also based on a convergence point wherein said convergence point comprises a point on said virtual display. 601 illustrates generating said right eye image for said right eye display is also based on said convergence point. 602 illustrates shifting said convergence point from a first point on said virtual display to a second point on said virtual display wherein said first point is different from said second point. 603 illustrates performing shifting of the convergence point based on at least one of the group consisting of: eye tracking of said user; head tracking of said user; and, controller.

Figure 7A:
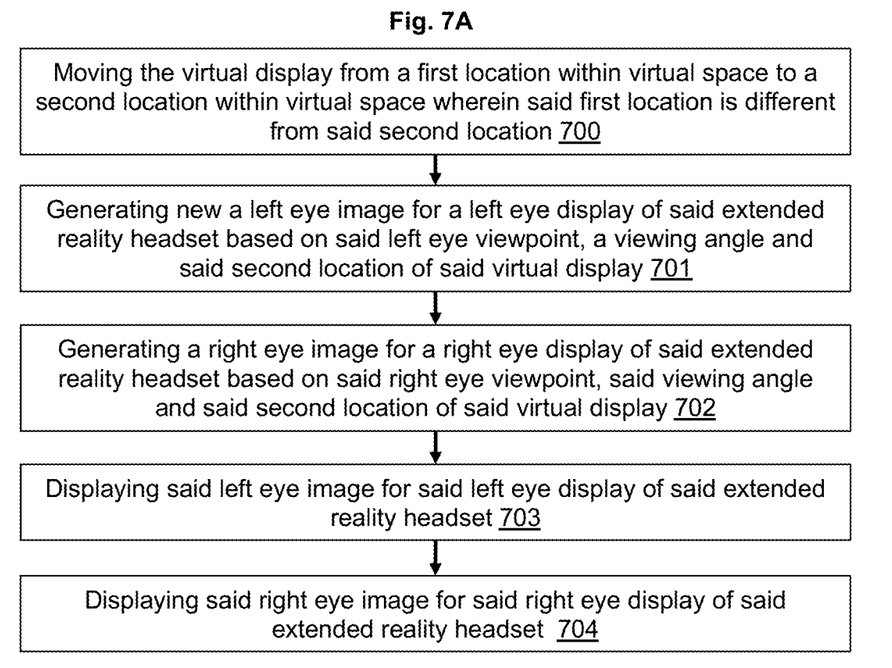
FIG. 7A illustrates moving a virtual double curved non-planar display using convergence within virtual space.

FIG. 7A illustrates moving a virtual double curved non-planar display using convergence within virtual space. 700 illustrates moving the virtual display from a first location within virtual space to a second location within virtual space wherein said first location is different from said second location. 701 illustrates generating new a left eye image for a left eye display of said extended reality headset based on said left eye viewpoint, a viewing angle and said second location of said virtual display. 702 illustrates generating a right eye image for a right eye display of said extended reality headset based on said right eye viewpoint, said viewing angle and said second location of said virtual display. 703 illustrates displaying said left eye image for said left eye display of said extended reality headset. 704 illustrates displaying said right eye image for said right eye display of said extended reality headset.

Figure 7B:
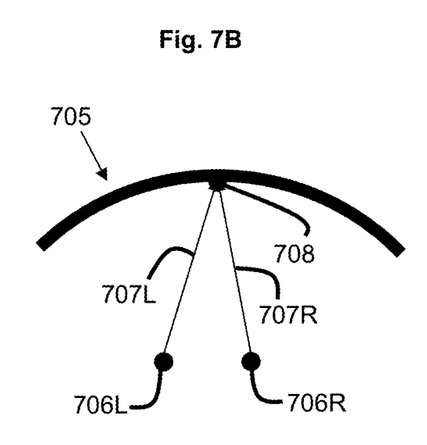
FIG. 7B illustrates viewing generating a first convergence point for the double curved non-planar display at a first time point.

FIG. 7B illustrates viewing generating a first convergence point for the double curved non-planar display at a first time point. 705 illustrates a top view of a cross section of a virtual double curved non-planar display. 706L illustrates the left eye view point at the first time point. 706R illustrates the right eye view point at the first time point. 707L is the look angle from the left eye viewpoint to convergence point 708 at the first time point. 707R is the look angle from the left eye viewpoint to convergence point 708 at the first time point.

Figure 7C:
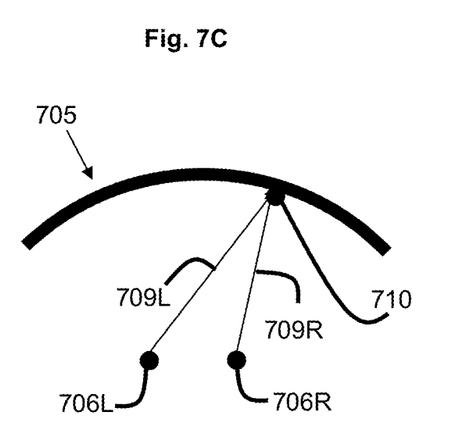
FIG. 7C illustrates viewing generating a second convergence point for the double curved non-planar display at a second time point.

FIG. 7C illustrates viewing generating a second convergence point for the double curved non-planar display at a second time point. 705 illustrates a top view of a cross section of a virtual double curved non-planar display. 706L illustrates the left eye view point at the first second point. 706R illustrates the right eye view point at the second time point. 709L is the look angle from the left eye viewpoint to convergence point 710 at the second time point. 709R is the look angle from the left eye viewpoint to convergence point 710 at the second time point. Thus, the convergence point is at different locations on the virtual display at different time points. Note that some of the areas on the screen could be shown in higher resolution than other portions of the screen, as described in Ser. No. 17/225,610 filed on Apr. 8, 2021, AN IMPROVED IMMERSIVE VIEWING EXPERIENCE, which is incorporated by reference in its entirety and Ser. No. 17/237,152 filed on Apr. 22, 2021, AN IMPROVED IMMERSIVE VIEWING EXPERIENCE, which is incorporated by reference in its entirety.

Figure 8A:
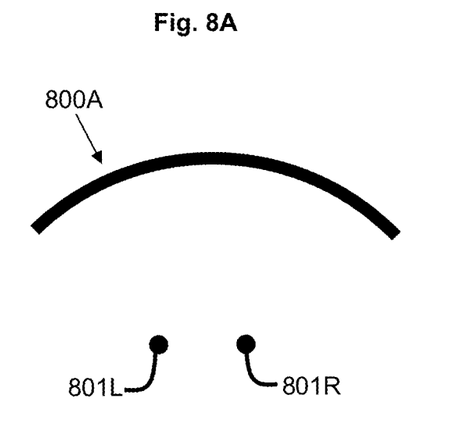
FIG. 8A illustrates a cross section of a top down view of a first size of a non-planar display for a first user.

FIG. 8A illustrates a cross section of a top down view of a first size of a non-planar display for a first user. 800A illustrates the horizontal curve of the non-planar display. Note that the vertical curve is not illustrated in this diagram. 801L illustrates the left eye viewpoint of a first user. 801R illustrates the right eye viewpoint of the first user.

Figure 8B:
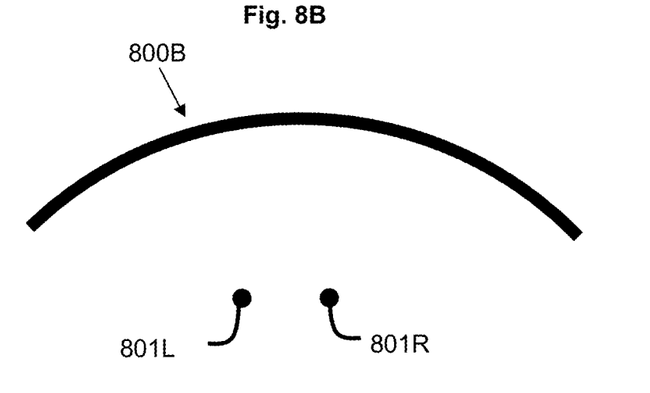
FIG. 8B illustrates a cross section of a top down view of a second size of a non-planar display for the first user.

FIG. 8B illustrates a cross section of a top down view of a second size of a non-planar display for the first user. 800B illustrates the horizontal curve of the non-planar display, which has been re-sized to meet the first user's desired re-configuration a different (larger in this case) curvature as compared to FIG. 8A. Note that the vertical curve is not illustrated in this diagram. 801L illustrates the left eye viewpoint of the first user. 801R illustrates the right eye viewpoint of the first user. Note that in this example, a modifiable horizontal radius of curvature is illustrated. Note that the modification of the horizontal radius of curvature can be made independently from the modification of the vertical radius of curvature. Alternatively, both the horizontal radius of curvature and the vertical radius of curvature can be made simultaneously.

Figure 9A:
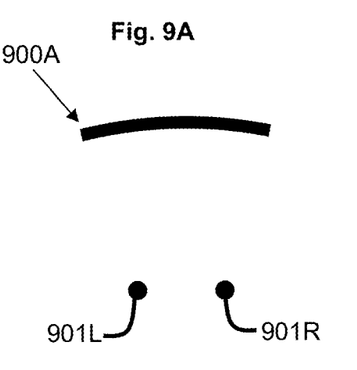
FIG. 9A illustrates a cross section of a top down view of a first shape of a non-planar display for a first user.

FIG. 9A illustrates a cross section of a top down view of a first shape of a non-planar display for a first user. 900A illustrates the horizontal curve of the non-planar display. Note that the vertical curve is not illustrated in this diagram. 901L illustrates the left eye viewpoint of a first user. 901R illustrates the right eye viewpoint of the first user. In this example, the non-planar display would subtend than 90 degrees of said user's horizontal field of view. This can be performed when said 2D image comprises one of the group consisting of: medical images (e.g., chest radiograph); text files (e.g., Microsoft Word file); and, internet webpages.

Figure 9B:
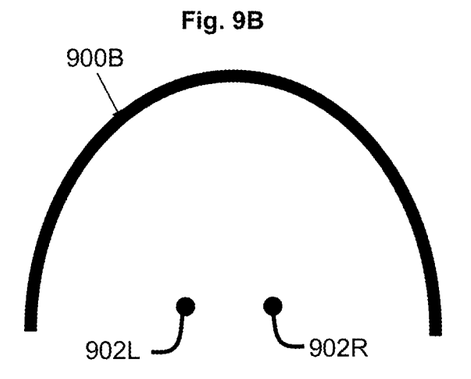
FIG. 9B illustrates a cross section of a top down view of a second shape of a non-planar display for a second user.

FIG. 9B illustrates a cross section of a top down view of a second shape of a non-planar display for a second user. 900B illustrates the horizontal curve of the non-planar display, which has been re-shaped to meet a second user's desired configuration a different curvature as compared to FIG. 9A. Note that the vertical curve is not illustrated in this diagram. 901L illustrates the left eye viewpoint of the second user. 901R illustrates the right eye viewpoint of the second user. Note that more 90 degrees of said user's horizontal field of view when said 2D image comprises a panoramic 2D image.

Figure 9C:
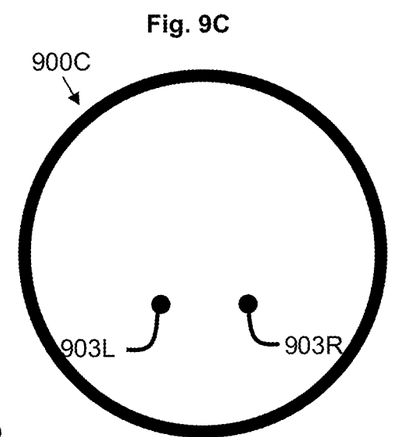
FIG. 9C illustrates a cross section of a top down view of a third shape of a non-planar display for a third user.

FIG. 9C illustrates a cross section of a top down view of a third shape of a non-planar display for a third user. 900C illustrates the horizontal curve of the non-planar display, which has been re-shaped to meet a third user's desired configuration a different curvature as compared to FIG. 9A and FIG. 9B. Note that the vertical curve is not illustrated in this diagram. 903L illustrates the left eye viewpoint of the third user. 903R illustrates the right eye viewpoint of the third user. Note that 360 degrees of said user's horizontal field of view when said 2D image comprises a 360 degree panoramic image wherein a cardinal direction that a user is facing matches that of said 360 degree panoramic image. This can be linked to a compass or a GPS system for improved navigation.

Figure 9D:
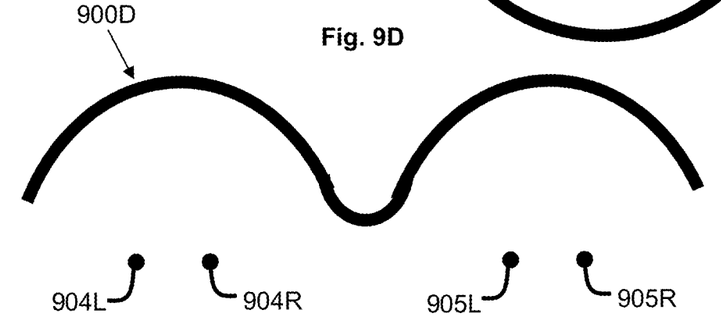
FIG. 9D illustrates a cross section of a top down view of a third shape of a non-planar display with multiple users.

FIG. 9D illustrates a cross section of a top down view of a third shape of a non-planar display with multiple users. 90D illustrates the horizontal curves of the non-planar display, which has been re-shaped to meet a multiple user configuration. Note that this concept could be extended to additional users. Note that this curvature is different as compared to FIG. 9A, FIG. 9B and FIG. 9C. Note that the vertical curve is not illustrated in this diagram. 904L illustrates the left eye viewpoint of the fourth user. 904R illustrates the right eye viewpoint of the fourth user. 905L illustrates the left eye viewpoint of the fifth user. 905R illustrates the right eye viewpoint of the fifth user. Note that the fourth user and the fifth user could both be watching the same portion of the same streaming video. Alternatively, the fourth user and the fifth user could be watching different portions of the same streaming video. Alternatively, the fourth user and the fifth user could be watching different streaming videos. Since they in this adjacent configuration, the fourth user could look over to see what the fifth user is watching and vice versa. Finally, note that a variety of shapes can be used including various irregular shapes, which can be used for entertaining mind games. Note that depending on the fifth user's position, some portions of the screen in front of the fourth user may not be well seen by the fifth user.

Figure 10A:
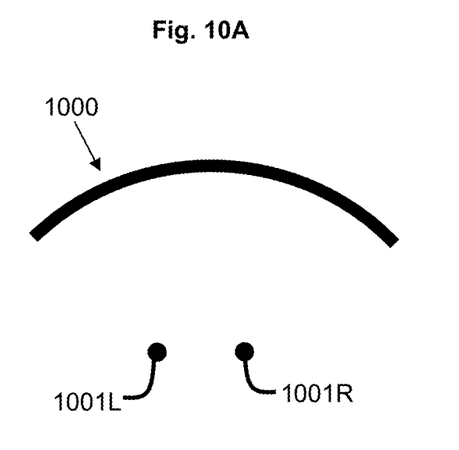
FIG. 10A illustrates a cross section of a top down view of a non-planar display in a first location and a user's first left eye viewpoint and the first user's first right eye viewpoint.

FIG. 10A illustrates a cross section of a top down view of a non-planar display in a first location and a user's first left eye viewpoint and the first user's first right eye viewpoint. 1000 illustrates the horizontal curve of the non-planar display in a first position. Note that the vertical curve is not illustrated in this diagram. 1001L illustrates a first left eye viewpoint of a user. 1001R illustrates a first right eye viewpoint of a user.

Figure 10B:
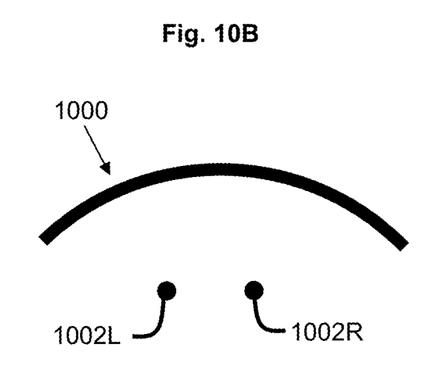
FIG. 10B illustrates a cross section of a top down view of a non-planar display in the first location and a user's shifted left eye viewpoint and the first user's shifted right eye viewpoint.

FIG. 10B illustrates a cross section of a top down view of a non-planar display in the first location and a user's shifted left eye viewpoint and the first user's shifted right eye viewpoint. 1000 illustrates the horizontal curve of the non-planar display in a first position. 1002L illustrates a shifted left eye viewpoint of a user. 1002R illustrates a shifted right eye viewpoint of a user.

Figure 10C:
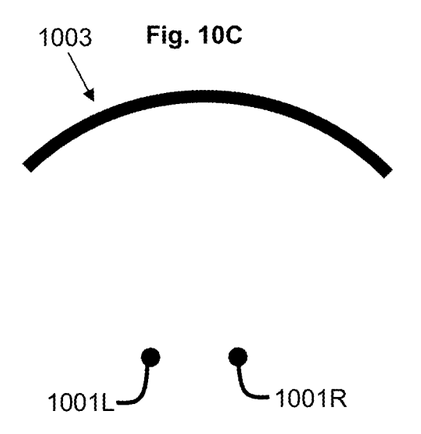
FIG. 10C illustrates a cross section of a top down view of a non-planar display in a shifted location and a user's first left eye viewpoint and the user's first right eye viewpoint.

FIG. 10C illustrates a cross section of a top down view of a non-planar display in a shifted location and a user's first left eye viewpoint and the user's first right eye viewpoint. 1003 illustrates the horizontal curve of the non-planar display in a shifted position. Note that that the orientation of the non-planar display can also be changed. Note that the vertical curve is not illustrated in this diagram. 1001L illustrates a first left eye viewpoint of a user. 1001R illustrates a first right eye viewpoint of a user. In this figure, the virtual display has been moved. In addition to changing the position of the left/right eye viewpoints, the inter-ocular distance can also be changed. The position and orientation of any of the following can be changed: left eye viewpoint; right eye viewpoint; viewing angle; convergence; and, the non-planar display.

Figure 11A:
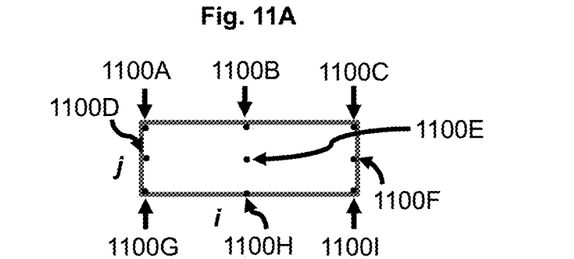
FIG. 11A illustrates a 2D image.

FIG. 11A illustrates a 2D image. This 2D image has a pixel array of 3000×1000. The bottom left pixel is labeled 1100A and would have (i,j) of (1,1). The bottom right pixel is labeled 1100B and would have (i,j) is of (3000,1). The top left pixel is labeled 1100C would have (i,j) of (1,1000). The top right pixel is labeled 1100D and would have (i,j) of (3000,1000). Note that the 2D image comprises an array of pixels wherein each pixel is characterized by an (i, j) coordinate and a value (color or grayscale). A frame of a 2D video.

Figure 11B:
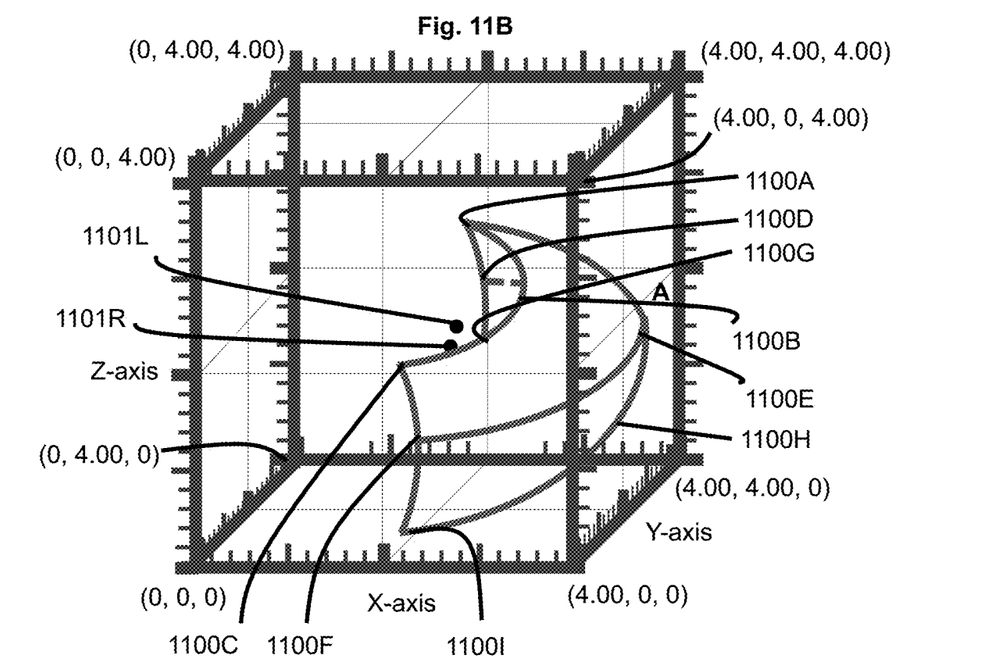
FIG. 11B illustrates mapping the 2D image onto a double curved virtual display.

FIG. 11B illustrates mapping the 2D image onto a double curved virtual display. For this scenario, the pixels in the 2D image would have coordinates in the virtual world, whether it be in augmented reality, mixed reality or virtual reality applications. The example shown here is an augmented reality application. A room measuring 4.00 meters×4.00 meters×4.00 meters is shown with each of the eight corners of the room marked. A left eye viewpoint 1101L is illustrated and in this example is located at a room coordinate of (2.00, 1.95, 1.00). A right eye viewpoint 1101R is illustrated and in this example is located at a room coordinate of (2.00, 2.05, 1.00). Each pixel in the 2D image above would be located at a 3D coordinate in the virtual world. Pixel 1100A is located at (2.00,3.50,1.50). Pixel 1100B is located at (3.50, 2.00,1.50). Pixel 1100C is located at (2.00,0.50,1.50). Pixel 1100D is located at (2.50,3.50,1.00). Pixel 1100E is located at (4.00,2.00,1.00). Pixel 1100F is located at (2.50,0.50, 1.00). Pixel 1100G is located at (2.00,3.50,0.50). Pixel 1100H is located at (3.50,2.00,0.50). Pixel 1100I is located at (2.00,0.50,0.50). Thus, each pixel in the 2D image is assigned an (x,y,z) coordinate.

Figure 11C:
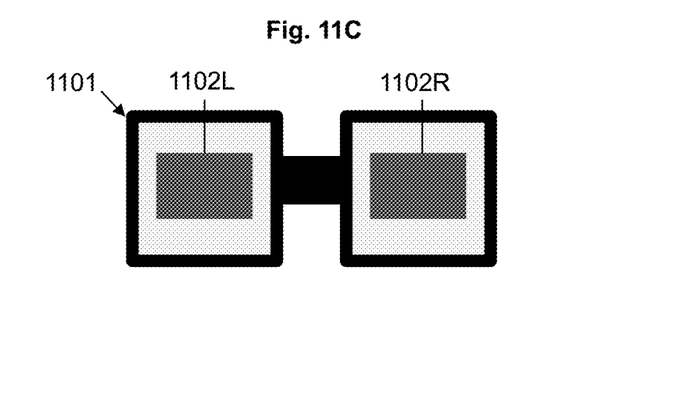
FIG. 11C illustrates rendering the double curved display onto an extended reality display unit.

FIG. 11C illustrates rendering the double curved display onto an extended reality display unit. 1101 illustrates an extended reality head display unit with a left eye display and a right eye display. 1102L illustrates the 2D image wherein each pixel has been mapped to an (x,y,z) coordinate and a left eye image is generated and display. 1102L illustrates the 2D image wherein each pixel has been mapped to an (x,y,z) coordinate and a right eye image is generated and display. Note that the images can be rendered per currently available techniques, such as U.S. Pat. No. 8,384,771, which is incorporated by reference in its entirety. In some embodiments, stretching of pixels can be performed. In some embodiments, variable sized pixels can be performed.

What is claimed is:

1. A method comprising:
  displaying a 2D image to a user on a non-planar display comprising:
    wherein said non-planar display comprises a top portion of said non-planar display that curves inwards towards said user's viewing position, a bottom portion of said non-planar display that curves inwards towards said user's viewing position, a left portion of said non-planar display that curves inward towards said user's viewing position, and a right portion of said non-planar display that curves inward towards said user's viewing position;
    wherein said non-planar display is a virtual display;
    wherein said virtual display has coordinates in virtual space;
    wherein said virtual display is presented to said user on an extended reality headset comprising at least one of the group of a virtual reality headset, an augmented reality headset or a mixed reality headset,
    wherein a left eye viewpoint is used for a left eye of said user;
    wherein a right eye viewpoint is used for a right eye of said user;
    wherein said left eye viewpoint and said right eye viewpoint are different viewpoints;
    wherein said left eye viewpoint and said right eye viewpoint are separated by an inter-ocular distance;
    wherein a left eye image for a left eye display of said extended reality headset is generated based on said left eye viewpoint, a viewing angle and said virtual display;
    wherein a right eye image for a right eye display of said extended reality headset is generated based on said right eye viewpoint, said viewing angle and said virtual display;
    wherein said left eye image for said left eye display of said extended reality headset is displayed;
    wherein said right eye image for said right eye display of said extended reality headset is displayed;
    wherein said left eye viewpoint is a first distance from a point on said virtual display;
    wherein a new left eye viewpoint is a second distance from said point on said virtual display;

wherein said first distance from said point on said virtual display to said left eye viewpoint is different than said second distance from said point on said virtual display to said new left eye viewpoint;

wherein said right eye viewpoint is said first distance from said point on said virtual display;

wherein a new right eye viewpoint is said second distance from said point on said virtual display;

wherein said first distance from said point on said virtual display to said right eye viewpoint is different than said second distance from said point on said virtual display to said new right eye viewpoint;

wherein a new left eye image for said left eye display of said extended reality headset is generated based on said new left eye viewpoint, a second viewing angle and said virtual display;

wherein a new right eye image for said left eye display of said extended reality headset is generated based on said new right eye viewpoint, said second viewing angle and said virtual display;

wherein said new left eye image for said left eye display of said extended reality headset is displayed; and wherein said new right eye image for said right eye display of said extended reality headset is displayed.

2. The method of claim 1 further comprising:
wherein said virtual display is presented on a second extended reality headset worn by a second user; and
wherein said second extended reality headset worn by said second user has a different location than said extended reality headset worn by said user.

3. The method of claim 1 further comprising wherein said 2D image is a frame of a 2D video.

4. The method of claim 1 further comprising:
wherein said virtual display has a first size;
wherein said 2D image has a first field of view;
wherein said virtual display is re-sized to a second virtual display;
wherein said second virtual display has a second size;
where said second size is larger than said first size;
wherein a second 2D image is presented on said second virtual display;
wherein said second 2D image has a second field of view; and
wherein said second field of view is larger than said first field of view.

5. The method of claim 1, further comprising:
wherein said non-planar display has a horizontal radius of curvature;
wherein said non-planar display has a vertical radius of curvature; and
wherein said horizontal radius of curvature is different from said vertical radius of curvature.

6. The method of claim 1 further comprising wherein, for each pixel of said 2D image, an (x, y, z) coordinate is assigned so that each pixel has an (x, y, z) coordinate in virtual space.

7. The method of claim 1 further comprising wherein said virtual display comprises less than 90 degrees of said user's horizontal field of view when said 2D image comprises one of the group comprising:
medical images;
text files; and
internet webpages.

8. The method of claim 1 further comprising wherein said virtual display comprises more 90 degrees of said user's horizontal field of view when said 2D image comprises a panoramic 2D image.

9. The method of claim 1 further comprising:
wherein said virtual display comprises 360 degrees of said user's horizontal field of view when said 2D image comprises a 360 degree panoramic image; and
wherein a cardinal direction that a user is facing matches that of said 360 degree panoramic image.

10. The method of claim 1 further comprising:
wherein said virtual display has a modifiable horizontal radius of curvature and a modifiable vertical radius of curvature; and
wherein said modifiable horizontal radius of curvature is modified independently from said modifiable vertical radius of curvature.

11. The method of claim 1 further comprising wherein an inertial measurement unit of said extended reality headset is configured to determine an orientation of said extended reality headset.

12. The method of claim 1 further comprising:
wherein a transmit/receive element of said extended reality headset is configured to receive signals front a set of transmitters in an area; and
wherein the received signals are used to compute a location of said extended reality headset within the area.

13. The method of claim 1 further comprising:
wherein a first portion of said virtual display is of a first resolution;
wherein a second portion of said virtual display is of a second resolution; and
wherein said first portion is different from said second portion.

14. The method of claim 1 further comprising:
wherein generating said left eye image for said left eye display is also based on a convergence point;
wherein generating said right eye image for said right eye display is also based on said convergence point; and
wherein said convergence point comprises a point on said virtual display.

15. The method of claim 14 further comprising:
wherein said convergence point is shifted from a first point on said virtual display to a second point on said virtual display; and
wherein said first point is different from said second point.

16. The method of claim 15 further comprising wherein said shift of said convergence point is performed based on at least one of the group consisting of:
eye tracking of said user; and
head tracking of said user.

17. The method of claim 1 further comprising:
wherein said virtual display moves from a first location within virtual space to a second location within virtual space;
wherein said first location is different from said second location;
generating an additional left eye image for said left eye display of said extended reality headset based on said new left eye viewpoint, third viewing angle and said second location of said virtual display;
generating an additional right eye image for said right eye display of said extended reality headset based on said new right eye viewpoint, said third viewing angle and said second location of said virtual display;

displaying said additional left eye image for said left eye display of said extended reality headset; and displaying said additional right eye image for said right eye display of said extended reality headset.

18. The method of claim 1 further comprising wherein said user wearing said extended reality headset and a second user wearing a second extended reality headset are view each other's virtual display.

19. An extended reality headset comprising:

a processor;

a left eye display operably connected to the processor;

a right eye display operably connected to the processor; and a non-transitory memory configurable to have computer-executable instructions stored thereupon, which when executed by the processor cause the extended reality headset to display a 2D image to a user on a non-planar display comprising:

wherein said non-planar display comprises a top portion of said non-planar display that curves inwards towards said user's viewing position, a bottom portion of said non-planar display that curves inwards towards said user's viewing position, a left portion of said non-planar display that curves inward towards said user's viewing position, and a right portion of said non-planar display that curves inward towards said user's viewing position;

wherein said non-planar display is a virtual display;

wherein said virtual display is at a first location;

wherein said virtual display is presented to said user on said extended reality headset;

wherein said extended reality headset comprises at least one of the group of a virtual reality headset, an augmented reality headset or a mixed reality headset;

wherein a left eye viewpoint is used for a left eye of said user;

wherein a right eye viewpoint is used for a right eye of said user;

wherein said left eye viewpoint and said right eye viewpoint are different viewpoints;

wherein said left eye viewpoint and said right eye viewpoint are separated by an inter-ocular distance;

wherein a left eye image for said left eye display of said extended reality headset is generated based on said left eye viewpoint, a viewing angle and said virtual display in said first location;

wherein a right eye image for said right eye display of said extended reality headset is generated based on said right eye viewpoint, said viewing angle and said virtual display in said first location;

wherein said left eye image for said left eye display of said extended reality headset is displayed;

wherein said right eye image for said right eye display of said extended reality headset is displayed;

wherein said virtual display moves from said first location within virtual space to a second location within virtual space;

wherein said first location is different from said second location;

wherein a new left eye image for said left eye display of said extended reality headset is generated based on said left eye viewpoint, a second viewing angle and said virtual display in said second location;

wherein a new right eye image for said right eye display of said extended reality headset is generated based on said right eye viewpoint said second viewing angle and said second location of said virtual display;

wherein said new left eye image for said left eye display of said extended reality headset is displayed; and wherein said new right eye image for said right eye display of said extended reality headset is displayed.

20. An extended reality headset comprising:

a processor;

a left eye display operably connected to the processor;

a right eye display operably connected to the processor; and a non-transitory memory configurable to have computer-executable instructions stored thereupon, which when executed by the processor cause the extended reality headset to display a 2D image on a non-planar display comprising:

wherein said non-planar display comprises a top portion of said non-planar display that curves inwards towards a user's viewing position, a bottom portion of said non-planar display that curves inwards towards said user's viewing position, a left portion of said non-planar display that curves inward towards said user's viewing position, and a right portion of said non-planar display that curves inward towards said user's viewing position, wherein said non-planar display is a virtual display;

wherein said virtual display has coordinates in virtual space;

wherein said virtual display is presented to said user on an extended reality headset comprising at least one of the group of a virtual reality headset, an augmented reality headset or a mixed reality headset;

wherein a left eye viewpoint is used for a left eye of said user;

wherein a right eye viewpoint is used for a right eye of said user;

wherein said left eye viewpoint and said right eye viewpoint are different viewpoints;

wherein said left eye viewpoint and said right eye viewpoint are separated by an inter-ocular distance;

wherein a left eye image for said left eye display of said extended reality headset is generated based on said left eye viewpoint, a viewing angle, a first convergence point and said virtual display;

wherein said first convergence point is at a first location on said virtual display;

wherein a right eye image for said right eye display of said extended reality headset is generated based on said right eye viewpoint, said viewing angle, said first convergence point and said virtual display;

wherein said left eye image for said left eye display of said extended reality headset is displayed;

wherein said right eye image for said right eye display of said extended reality headset is displayed;

wherein said left eye viewpoint is a first distance from said convergence point on said virtual display;

wherein a new left eye viewpoint is a second distance to said convergence point on said virtual display;

wherein said first distance from said convergence point to said left eye viewpoint is different from said second distance from said convergence point to said new left eye viewpoint;

wherein said right eye viewpoint is a first distance from said convergence point on said virtual display;

wherein a new right eye viewpoint is a second distance to said convergence point on said virtual display;

wherein said first distance from said convergence point to said right eye viewpoint is different from said second distance from said convergence point to said right left eye viewpoint;

wherein a new left eye image for said left eye display of said extended reality headset is generated based on said new left eye viewpoint, a second viewing angle, a second convergence point and said virtual display;

wherein said second convergence point is at a second location on said virtual display;

wherein said second location on said virtual display is different from said first location on said virtual display;

wherein a new right eye image for said right eye display of said extended reality headset is generated based on said new right eye viewpoint, said second viewing angle, said second convergence point and said virtual display;

wherein said new left eye image for said left eye display of said extended reality headset is displayed; and wherein said new right eye image for said right eye display of said extended reality headset is displayed.

* * * * *